(12) United States Patent
Smit et al.

(10) Patent No.: US 8,623,945 B2
(45) Date of Patent: Jan. 7, 2014

(54) USE OF OLIGOMERIC CARBODIIMIDES AS STABILIZERS

(75) Inventors: Theo Smit, Heidelberg (DE); Laurence Pottie, Köln (DE); Simone Schillo, Ludwigshafen (DE); Volker Frenz, Altleiningen (DE); Roelof van der Meer, Halsteren (NL)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/421,363

(22) Filed: Mar. 15, 2012

(65) Prior Publication Data
US 2012/0238676 A1 Sep. 20, 2012

Related U.S. Application Data

(60) Provisional application No. 61/454,016, filed on Mar. 18, 2011.

(51) Int. Cl.
*C08K 5/3412* (2006.01)
*C07D 413/12* (2006.01)
*C08K 5/3415* (2006.01)
*C08K 5/353* (2006.01)

(52) U.S. Cl.
USPC .......... 524/95; 524/98; 524/104; 540/525; 548/238; 548/520

(58) Field of Classification Search
USPC ........ 524/95, 98, 104; 540/525; 548/238, 520
See application file for complete search history.

(56) References Cited

U.S. PATENT DOCUMENTS

| 5,439,952 | A | 8/1995 | Lum et al. | |
| 5,498,747 | A * | 3/1996 | Pohl et al. | 560/25 |
| 6,984,694 | B2 | 1/2006 | Blasius, Jr. et al. | |
| 2004/0138381 | A1* | 7/2004 | Blasius et al. | 525/131 |
| 2011/0306718 | A1 | 12/2011 | Scherzer et al. | |
| 2012/0016090 | A1 | 1/2012 | Loos et al. | |

FOREIGN PATENT DOCUMENTS

| DE | 32 17 440 | A1 | 11/1983 | |
| DE | 19622610 | * | 12/1997 | ........... C07D 211/46 |
| DE | 198 09 634 | A1 | 9/1999 | |
| EP | 0 507 407 | A1 | 10/1992 | |
| EP | 0 628 541 | A1 | 12/1994 | |
| EP | 798322 | * | 1/1997 | ............. C08G 18/02 |
| EP | 0 940 389 | A2 | 9/1999 | |
| WO | WO 2005/111048 | A1 | 11/2005 | |
| WO | WO 2011/054701 | A1 | 5/2011 | |

OTHER PUBLICATIONS

Machine translation of EP 798322. Jan. 1997.*
U.S. Appl. No. 13/676,396, filed Nov. 14, 2012, Pottie, et al.
International Search Report issued Nov. 15, 2012 in Application No. PCT/EP2012/054550 (With English Translation of Category of Cited Documents).

* cited by examiner

*Primary Examiner* — John Uselding
(74) *Attorney, Agent, or Firm* — Oblon, Spivak, McClelland, Maier & Neustadt, L.L.P.

(57) ABSTRACT

This invention relates to a process for stabilizing polymers with oligomeric carbodiimides containing at least one heterocyclic end group and stabilizers. The oligomeric carbodiimides may be compounds of the general formula (I):

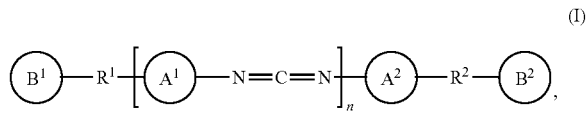

where $A^1$, $A^2$ are each independently, identically or differently, hydrocarbon groups having 2 to 20 carbon atoms, $B^1$, $B^2$ are each independently, identically or differently, heterocycles, $C_1$-$C_{30}$-alcohols, polyetherols, polyesterols, amines, polyether amines, polyester amines, thioalcohols, polyether thiols, polyester thiols; $R^1$, $R^2$ are each independently, identically or differently:

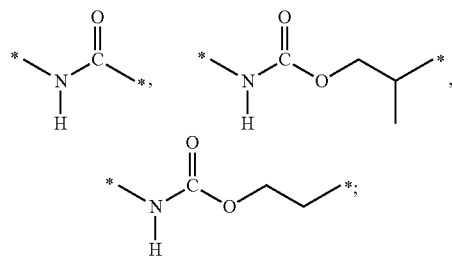

n is an integer from 2 to 100, and $A^1$, $A^2$, $B^1$ and $B^2$ may each be substituted at any desired position by $C_1$-$C_{20}$-alkyl, $C_2$-$C_{20}$-alkenyl, $C_2$-$C_{20}$-alkynyl, $C_1$-$C_{20}$-alkoxy, carbonyl oxygen (=O) or halogen, with the proviso that at least one $B^1$ or $B^2$ substituent is a heterocyclic end group. The invention also relates to compositions of the oligomeric carbodiimides and mixtures.

15 Claims, No Drawings

USE OF OLIGOMERIC CARBODIIMIDES AS STABILIZERS

CROSS-REFERENCE TO RELATED APPLICATIONS

This application claims the benefit of priority under Section 119(e) of U.S. Provisional Application No. 61/454,016, filed on Mar. 18, 2011.

BACKGROUND OF THE INVENTION

The present invention relates to the use of oligomeric carbodiimides comprising at least one heterocyclic end group as stabilizers for polymers. The invention further relates to processes for stabilizing polymers against hydrolysis by adding oligomeric carbodiimides. The invention further provides selected carbodiimides and mixtures comprising oligomeric carbodiimides, further additives and/or polymers.

Further embodiments of the present invention will be apparent from the claims, the description and the examples. It would be appreciated that the features of the invention subject matter which are recited hereinabove and which are yet to be elucidated hereinbelow can be used not only in the particular concrete combination recited but also in other combinations without departing the scope of the invention. Embodiments of the present invention where all the features of the invention subject matter have the preferred and very preferred meanings are more particularly also preferred and very preferred, respectively.

Monomeric carbodiimides are known for use as hydrolysis stabilizers (U.S. Pat. No. 5,439,952). However, their use frequently gives rise to toxic by-products such as phenyl isocyanates. Oligomeric or polymeric carbodiimides are used in order to avoid toxicity issues.

DE 3217440 for example describes polyethylene terephthalates having improved resistance to hydrolysis and they comprise polycarbodiimides.

DE 198 09 634 A1 describes processes for preparing carbodiimides and mixtures comprising carbodiimides and polyesters or polyurethanes.

Carbodiimides comprising silane groups attached via urea groups and also mixtures thereof with polymers are described in WO 2005/111048 A1.

EP 0 507 407 A1 describes multifunctional water-dispersible crosslinking agents based on oligomeric substances comprising carbodiimide and other reactive functional groups, for example heterocycles. Aqueous dispersions, emulsions or solutions of such crosslinking agents and also processes for preparing the crosslinking agents are also described.

Oligomeric or polymeric carbodiimides are believed to be less toxic than monomeric carbodiimides because of lower by-product volatility. However, oligomeric or polymeric carbodiimides are frequently also less stabilizing than monomeric carbodiimides.

The present invention therefore has for its object to provide stabilizers on the basis of carbodiimides that do not have the abovementioned issues. It is more particularly an object of the present invention to provide carbodiimides that have a comparable stabilizing effect to monomeric carbodiimides without having the toxic potential of the latter.

BRIEF SUMMARY OF THE INVENTION

We have found that these objects are achieved by the use of oligomeric carbodiimides comprising at least one heterocyclic end group, as stabilizers for polymers.

DETAILED DESCRIPTION OF THE INVENTION

Expressions of the form $C_a$-$C_b$ in the context of this invention identify chemical compounds or substituents having a certain number of carbon atoms. The number of carbon atoms can be selected from the entire range from a to b, including a and b, a is at least one and b is always greater than a. The chemical compounds or the substituents are further specificized by expressions of the form $C_a$-$C_b$-V. V here stands for a chemical class of compounds or class of substituents, for example for alkyl compounds or alkyl substituents.

Halogen is fluorine, chlorine, bromine or iodine, preferably fluorine, chlorine or bromine and more preferably fluorine or chlorine.

Specifically, the collective terms recited for the various substituents have the following meanings:

$C_1$-$C_{20}$-Alkyl: straight-chain or branched hydrocarbon moieties having up to 20 carbon atoms, for example $C_1$-$C_{10}$-alkyl or $C_{11}$-$C_{20}$-alkyl, preferably $C_1$-$C_{10}$-alkyl for example $C_1$-$C_3$-alkyl, such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,3,3-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl and also isomers thereof.

$C_2$-$C_{20}$-Alkenyl: unsaturated, straight-chain or branched hydrocarbon moieties having 2 to 20 carbon atoms and a double bond in any desired position, for example $C_2$-$C_{10}$-alkenyl or $C_{11}$-$C_{20}$-alkenyl, preferably $C_2$-$C_{10}$-alkenyl such as $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, and also $C_7$-$C_{10}$-alkenyl, such as the isomers of heptenyl, octenyl, nonenyl or decenyl.

$C_2$-$C_{20}$-Alkynyl: straight-chain or branched hydrocarbon groups having 2 to 20 carbon atoms and a triple bond in any desired position, for example $C_2$-$C_{10}$-alkynyl or $C_{11}$-$C_{20}$-alkynyl, preferably $C_2$-$C_{10}$-alkynyl such as $C_2$-$C_4$-alkynyl, such as ethynyl, 1-propynyl, 2-propynyl, 1-butynyl, 2-butynyl, 3-butynyl, 1-methyl-2-propynyl, or $C_5$-$C_7$-alkynyl, such as 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl and also $C_7$-$C_{10}$-alkynyl, such as the isomers heptynyl, octynyl, nonynyl, decynyl.

$C_3$-$C_{15}$-Cycloalkyl: monocyclic, saturated hydrocarbon groups having 3 up to 15 carbon ring members, preferably $C_3$-$C_8$-cycloalkyl such as cyclopropyl, cyclobutyl, cyclopentyl, cyclohexyl, cycloheptyl or cyclooctyl and also a saturated or unsaturated cyclic system such as, for example, norbornyl or norbenyl.

Aryl: a mono- to trinuclear aromatic ring system comprising 6 to 14 carbon ring members, for example phenyl, naphthyl or anthracenyl, preferably a mono- to binuclear and more preferably a mononuclear aromatic ring system.

$C_1$-$C_{20}$-Alkoxy is a straight-chain or branched alkyl group having 1 to 20 carbon atoms (as recited above) which are attached via an oxygen atom (—O—), for example $C_1$-$C_{10}$-alkoxy or $C_{11}$-$C_{20}$-alkoxy, preferably $C_1$-$C_{10}$-alkyloxy, more preferably $C_1$-$C_3$-alkoxy, for example methoxy, ethoxy, propoxy.

Heteroatoms are phosphorus, oxygen, nitrogen or sulfur preferably oxygen, nitrogen or sulfur, the free valences of which are optionally saturated by hydrogen atoms.

The symbol "*" in the context of the present invention identifies in all chemical compounds the valence via which any one chemical group is attached to some other chemical group.

In one preferable embodiment of the invention, the oligomeric carbodiimides comprising at least one heterocyclic end group are used as hydrolysis stabilizers or acid traps for polymers.

Oligomeric carbodiimides comprising at least one heterocyclic end group are obtainable by processes known to a person skilled in the art. The preparation of such carbodiimides is described for example in the abovementioned reference EP 0 507 407 A1. A general process for preparing the oligomeric carbodiimides comprising at least one heterocyclic end group comprises for example reacting a diisocyanate with a polyetherol and a heterocycle.

The oligomeric carbodiimides used in the context of the invention are preferably compounds of the general formula (I),

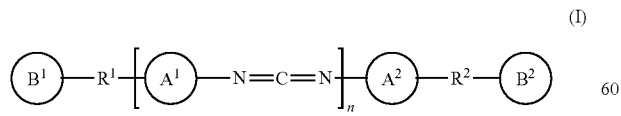

where
A¹, A² are each independently, identically or differently, hydrocarbon groups having 2 to 20 carbon atoms, and preferably comprise cyclic hydrocarbon moieties, especially $C_3$-$C_{15}$-cycloalkylene or arylene;

B¹, B² are each independently, identically or differently, heterocycles, $C_1$-$C_{30}$-alcohols, polyetherols, polyesterols, amines, polyether amines, polyester amines, thioalcohols, polyether thiols, polyester thiols, preferably heterocycles, $C_1$-$C_{30}$-alcohols, polyetherols, polyesterols, most preferably heterocycles;

R¹, R² are each independently, identically or differently

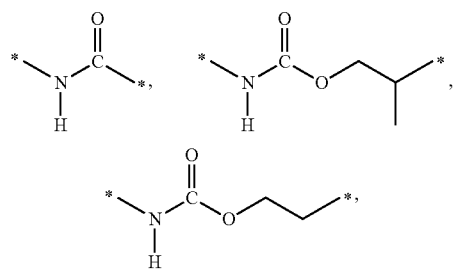

preferably

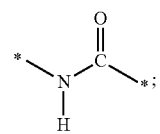

n is an integer from 2 to 100, preferably from 2 to 50,
more preferably from 2 to 20,
and especially from 2 to 10,
and where A¹, A², B¹ and B² may each be substituted at any desired position by $C_1$-$C_{20}$-alkyl, $C_2$-$C_{20}$-alkenyl, $C_2$-$C_{20}$-alkynyl, $C_1$-$C_{20}$-alkoxy, carbonyl oxygen (=O) or halogen, preferably $C_1$-$C_4$-alkyl,
with the proviso that at least one B¹ or B² substituent is a heterocyclic end group.

In a further preferable embodiment, the A¹, A² substituents of the carbodiimides comprise the hydrocarbon groups

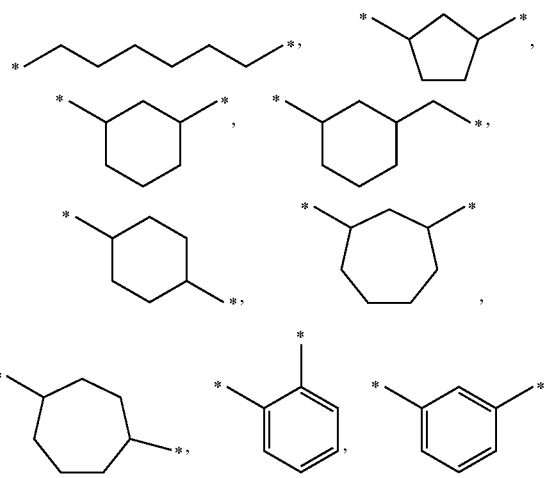

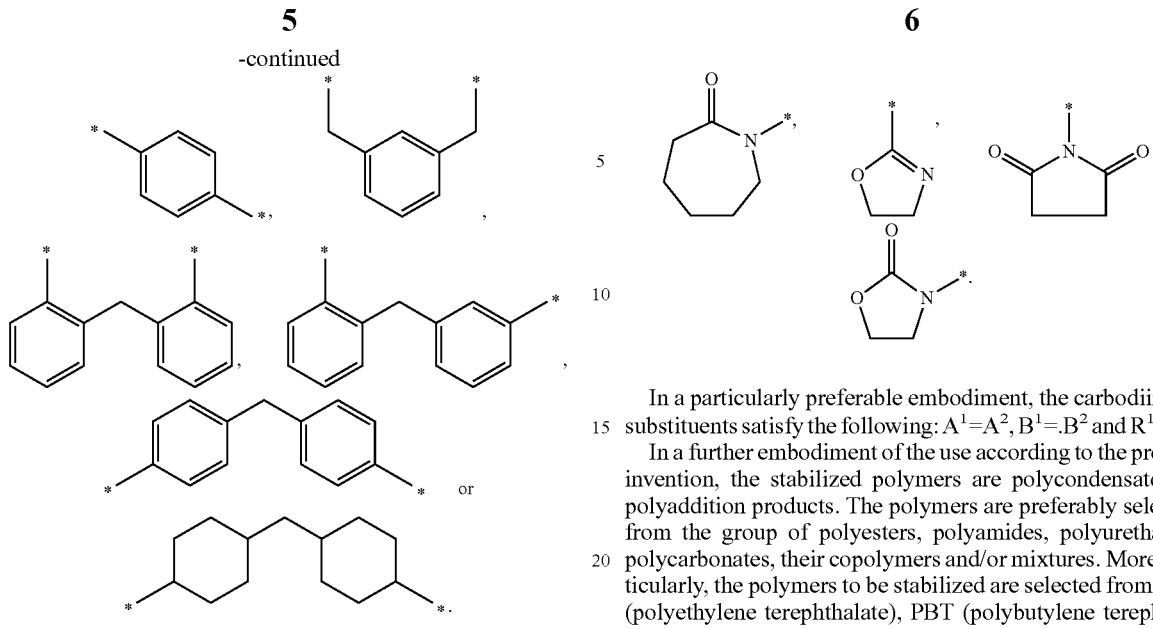

The A1, A2 substituents of the carbodiimides preferably comprise the hydrocarbon groups

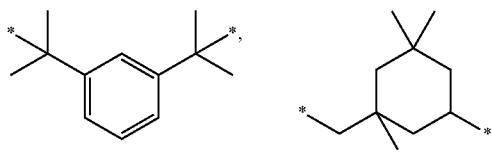

In a further preferable embodiment of the use according to the present invention, the $B^1$, $B^2$ substituents of the carbodiimides are selected from the group of three- to twelve-membered, preferably three- to nine-membered and more preferably five to seven-membered ring systems (heterocycles, heterocyclic end groups) having oxygen, nitrogen and/or sulfur atoms and one or more rings, such as aziridine, epoxide, thiirane, azirine, oxirene, thiirene, azetidine, oxetane, thietane, beta-lactam, beta-lactone, thiethanone, furan, pyrroline, dihydrofuran, dihydrothiophene, pyrrolidine, tetrahydrofuran, tetrahydrothiophene, oxazolidine, dioxolane, oxathiolane, thiazolidine, imidazoline, dithiolane, pyrazolidine, pyrazoline, oxazoline, thiazoline, imidazoline, dioxole, oxazolone, pyrrolidone, butyrolactone, thiobutyrolactone, butyrothiolactone, thiobutyrothiolactone, oxazolidone, dioxolan-2-one, thiazolidinone, dihydropyridine, tetrahydropyridine, pyran, dihydropyran, tetrahydropyran, succinic anhydride, succinimide, thiopyran, dihydrothiopyran, tetrahydrothiopyran, dihydropyrimidine, tetrahydropyrimidine, hexahydropyrimidine, dioxane, morpholine, thiamorpholine, dithiane, triazine, wherein these are chemically attached to $R^1$ or $R^2$ in any desired manner, for example via a bond to a carbon atom of the heterocycle or a bond to one of the heteroatoms.

Particular preference is given to five-, six- or seven-membered saturated nitrogen-containing ring systems which are attached to $R^1$ or $R^2$ via a ring nitrogen atom or ring carbon atom and which may further comprise one or two further nitrogen atoms or oxygen atoms. These are most preferably selected from the group of In a particularly preferable embodiment, the carbodiimide substituents satisfy the following: $A^1=A^2$, $B^1=B^2$ and $R^1=R^2$.

In a further embodiment of the use according to the present invention, the stabilized polymers are polycondensates or polyaddition products. The polymers are preferably selected from the group of polyesters, polyamides, polyurethanes, polycarbonates, their copolymers and/or mixtures. More particularly, the polymers to be stabilized are selected from PET (polyethylene terephthalate), PBT (polybutylene terephthalate), PEN (polyethylene naphthalate), PC (polycarbonate), ABS (acrylonitrile-butadiene-styrene copolymer), biodegradable aliphatic-aromatic copolyesters, biopolymers or PA6 (nylon-6). Useful biodegradable aliphatic-aromatic copolyesters are particularly poly(butylene adipate-co-terephthalate)s and useful biopolymers include particularly PLA (polylactic acid) and PHA (polyhydroxyalkanoates). PC-ABS mixtures are useful as mixtures in particular. The stabilized polymers self-evidently also comprise recycled or reprocessed polymers.

The present invention further provides a process for stabilizing polymers against hydrolysis, which process comprises adding an effective amount of the above-recited oligomeric carbodiimides, preferably an effective amount of the carbodiimides of the general formula (I), to the polymer.

In a preferable embodiment of the process according to the present invention, the oligomeric carbodiimides are added to the polymer in an amount of 0.01 to 10 wt %, preferably of 0.1 to 5 wt % and especially of 0.1 to 2 wt % based on the total amount of polymer and oligomeric carbodiimide.

Incorporating the oligomeric carbodiimides comprising at least one heterocyclic end group into the polymers is generally effected by mixing the constituent parts. For example, the mixing is effected by processes known to a person skilled in the art which are of the type generally used in the additization of polymers. The oligomeric carbodiimides in solid, liquid or dissolved form are preferably used for additizing polyaddition or polycondensation polymers. The oligomeric carbodiimides can be incorporated in the polymers for this purpose by the customary methods not only as a solid or liquid formulation but also as a powder. Examples which may be mentioned here include mixing the carbodiimides with the polymers before or during an extrusion step, kneading, calendering, film/sheet extrusion, fiber extrusion or blow molding. Mixing the constituent parts before incorporation, with or without assistance of a solvent, is possible. The solvent can optionally be removed before the incorporating step. Further examples of additizing or stabilizing polymers with additives are discernible from the Plastics Additives Handbook, 5th edition, Hanser Verlag, ISBN 1-56990-295-X. The additized polymers can be in the form of granules, pellets, powders, self-supporting films/sheets or fibers.

Polymeric moldings comprising oligomeric carbodiimides comprising at least one heterocyclic end group are produced by processes known to the person skilled in the art. More particularly, the polymeric moldings are obtainable by extrusion or coextrusion, compounding, processing of granules or pellets, injection molding, blow molding or kneading. Processing is preferably by extrusion or coextrusion into films/sheets (cf. Saechtling Kunststoff Taschenbuch, 28th edition, Karl Oberbach, 2001).

The polymers or polymeric moldings may additionally comprise at least one further, frequently commercially available, additive preferably selected from chain extenders, colorants, antioxidants, other stabilizers, e.g., hindered amine light stabilizers HALS, UV absorbers, nickel quenchers, metal deactivators, reinforcing and filler materials, antifoggants, biocides, acid traps, antistats, IR absorbers for longwave IR radiation, antiblocking agents such as SiO2, light scatterers such as MgO or TiO2, organic or inorganic reflectors (aluminum flakes for example). Preference for use as additional additives is given to chain extenders, especially epoxy-containing functionalized styrene-(meth)acrylic ester copolymers based on epoxy-containing (meth)acrylic ester monomers combined with styrene and/or (meth)acrylic ester monomers, as described for example in U.S. Pat. No. 6,984,694.

The oligomeric carbodiimides comprising at least one heterocyclic end group are therefore preferably used according to the present invention as stabilizers for polymers in combination with chain extenders, especially epoxy-containing functionalized styrene-(meth)acrylic ester copolymers. The invention further provides processes for stabilizing polymers against hydrolysis by adding oligomeric carbodiimides.

A further preferred embodiment of the invention is a process for stabilizing polymers, especially against hydrolysis, wherein an effective amount of epoxy-containing functionalized styrene-(meth)acrylic ester copolymers is added to the polymer in addition to the oligomeric carbodiimides comprising at least one heterocyclic end group. In a preferable embodiment of the process according to the present invention, the epoxy-containing functionalized styrene-(meth)acrylic ester copolymers are added to the polymer in an amount of 0.01 to 5 wt %, preferably of 0.1 to 3 wt % and especially of 0.2 to 2 wt % based on the total amount of polymer and oligomeric carbodiimide. The oligomeric carbodiimides comprising at least one heterocylic end group and the epoxy-containing functionalized styrene-methacrylic ester copolymers can here be added to the polymer separately from each other or as a mixture. The addition to the polymer can take place simultaneously or in succession.

The invention further provides mixtures comprising oligomeric carbodiimides comprising at least one heterocyclic end group, especially those of the general formula (II) and chain extenders, wherein epoxy-containing functionalized styrene-(meth)acrylic ester copolymers are preferable as chain extenders. The ratio of oligomeric carbodiimides comprising at least one heterocyclic end group to chain extenders can vary within wide limits depending on the intended use. The ratio in such mixtures of oligomeric carbodiimides comprising at least one heterocyclic end group to epoxy-containing functionalized styrene-(meth)acrylic ester copolymers is preferably in the range from 99.9:0.01 to 0.01:99.9, preferably in the range from 90:10 to 10:90 and more preferably in the range from 80:10 to 10:80.

In a further preferred aspect, the invention provides mixtures comprising oligomeric carbodiimides comprising at least one heterocyclic end group, especially those of the general formula (II), chain extenders, wherein epoxy-containing functionalized styrene-(meth)acrylic ester copolymers are preferable as chain extenders, and polymers. Such mixtures preferably comprise from 0.01 to 15 and preferably from 0.2 to 15 wt % of oligomeric carbodiimides comprising at least one heterocyclic end group, from 0.01 to 30 and preferably from 0.2 to 30 wt % of epoxy-containing functionalized styrene-(meth)acrylic ester copolymers and from 55 to 99.98 and preferably from 55 to 99.6 wt % of polymers, all based on the total amount of oligomeric carbodiimide comprising at least one heterocyclic end group, chain extenders and polymer. The polymers here are preferably selected from the group of polyesters, polyamides, polyurethanes, polycarbonates, their copolymers and/or mixtures. More particularly, the polymers to be stabilized are selected from PET (polyethylene terephthalate), PBT (polybutylene terephthalate), PEN (polyethylene naphthalate), PC (polycarbonate), ABS (acrylonitrile-butadiene-styrene copolymer), biodegradable aliphatic-aromatic copolyesters, biopolymers or PA6 (nylon-6). Useful biodegradable aliphatic-aromatic copolyesters are particularly poly(butylene adipate-co-terephthalate)s and useful biopolymers include particularly PLA (polylactic acid) and PHA (polyhydroxyalkanoates). PC-ABS mixtures are useful as mixtures in particular.

The invention further provides selected oligomeric carbodiimides of the general formula

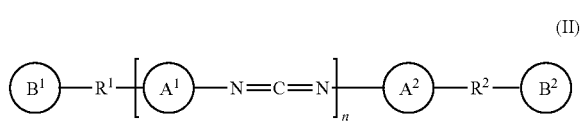

where
A$^1$, A$^2$ each comprise the groups

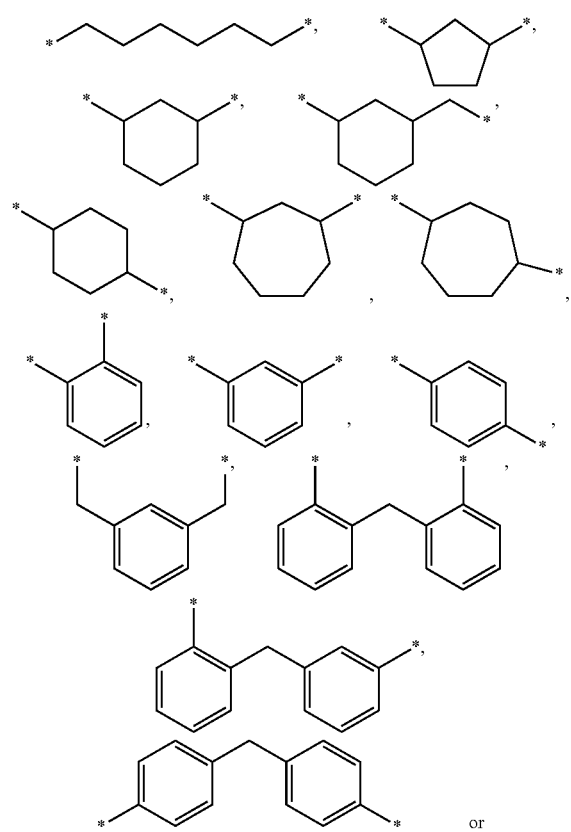

or

-continued

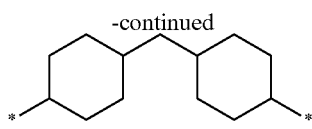

preferably

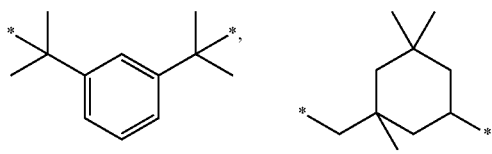

independently, identically or differently.

$B^1$, $B^2$ are each independently, identically or differently, $R^3$—(O—$CH_2$—$CHR^4$)$_m$—O—*,

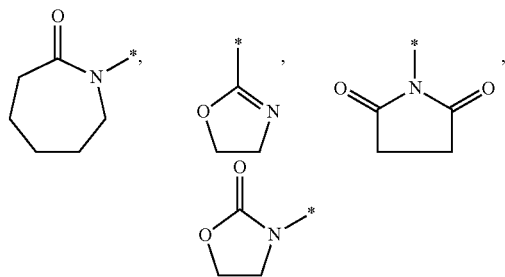

and
$R^1$, $R^2$ are each independently, identically or differently,

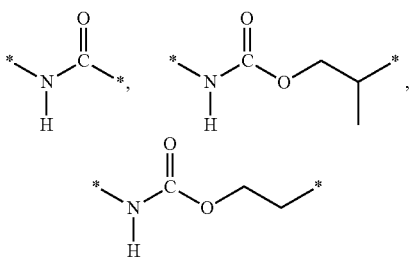

preferably

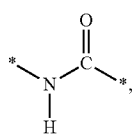

and
n is an integer from 2 to 100, preferably from 2 to 50, more preferably from 2 to 20,
and more particularly from 2 to 10
and
$R^3$ is $C_1$-$C_{20}$-alkyl, $C_2$-$C_{20}$-alkenyl, $C_2$-$C_{20}$-alkynyl, preferably $C_1$-$C_4$-alkyl,
$R^4$ is H, $C_1$-$C_{20}$-alkyl, $C_2$-$C_{20}$-alkenyl, $C_2$-$C_{20}$-alkynyl, preferably H, $C_1$-$C_4$-alkyl, and
m is an integer from 1 to 500, and preferably from 1 to 100, 1 to 50,
and where $A^1$, $A^2$, $B^1$ and $B^2$ may each be substituted at any desired position by $C_1$-$C_{20}$-alkyl, $C_2$-$C_{20}$-alkenyl, $C_2$-$C_{20}$-alkynyl, $C_1$-$C_{20}$-alkoxy, carbonyl oxygen (=O) or halogen, preferably $C_1$-$C_4$-alkyl,
with the proviso that at least one $B^1$ or $B^2$ substituent is a heterocyclic end group.

The invention further provides mixtures comprising oligomeric carbodiimides of the general formula (II) and polymers, wherein the polymers are preferably polycondensates or polyaddition products. The polymers also comprise recycled or reprocessed polymers. The polymers here are preferably selected from the group of polyesters, polyamides, polyurethanes, polycarbonates and copolymers thereof and especially the polymers are PET, PBT, PEN, PC, ABS, biodegradable aliphatic-aromatic copolyesters, biopolymers or PA6. Useful biodegradable aliphatic-aromatic copolyesters are particularly poly(butylene adipate-co-terephthalate)s and useful biopolymers include particularly PLA and PHA. PC-ABS mixtures are useful as mixtures in particular.

In one preferable embodiment, the oligomeric carbodiimides are comprised in the mixture in an amount of 0.01 to 10 wt %, preferably of 0.1 to 5 wt % and especially of 0.1 to 2 wt % based on the total amount of polymer and oligomeric carbodiimide.

The present invention provides oligomeric carbodiimides for polymer stabilization which, owing to their oligomeric structure, have little toxicity in handling, incorporation and use as a stabilizer, especially as a hydrolysis stabilizer or acid trap. At the same time, because of their functionalization with at least one heterocyclic end group, the oligomeric carbodiimides ensure efficient and effective polymer stabilization. Especially used as hydrolysis stabilizers for polyaddition and polycondensation polymers, the oligomeric carbodiimides used in the context of the present invention display outstanding properties.

The examples which follow are provided to illustrate the invention without limiting the subject matter of the invention.

EXAMPLES

Example 1

Synthesizing an Oligomeric Carbodiimide 120 grams of isophorone diisocyanate were heated to 90° C. in a stirred flask equipped with a thermometer and a dropping funnel. 24.3 grams of Pluriol A 500 E (polyethylene glycol with molecular weight (number average) of about 500 g/mol) were added thereto. After 9 hours, the NCO content of the mixture had dropped to 29.8 wt %. Thereafter, 0.24 gram of a mixture of 1-methyl-1-phospha-2-cyclopentene 1-oxide and 1-methyl-1-phospha-3-cyclopentene 1-oxide was added, a pressure of 200 mbar was applied and the reaction mixture was heated to 145° C. After 12 hours, the mixture had reached an NCO content of 4.3 wt %. The remaining NCO groups were converted by addition of 15.2 grams of caprolactam.

Reaction product: CDI1

Analysis: IR-ATR: C=O 1650 cm$^{-1}$, N=C=N 2116 cm$^{-1}$

Example 2

Acid Trap

The four oligomeric carbodiimides functionalized with heterocyclic end groups and listed in table 1 were prepared.

TABLE 1

Structure of functionalized oligomeric carbodiimides (CDI1-4)

| oligomeric carbodiimide group | $R^{10}$ and $R^{11}$ are Pluriol A 500 E or: |
|---|---|
| [structure: aliphatic isophorone-based oligomeric carbodiimide with $R^{10}$ and $R^{11}$ end-capping urethane groups, repeat unit n] | [caprolactam-derived N-linked group] CDI1 |
| | [2-(oxazolin-2-yl)propoxy group] CDI2 |
| | [N-(2-ethoxy)succinimide group] CDI3 |
| [structure: aromatic oligomeric carbodiimide based on tetramethylxylylene diisocyanate with $R^{10}$ and $R^{11}$ urethane end groups, repeat unit n] | [N-(2-ethoxy)oxazolidinone group] CDI4 |

The n value in the oligomeric carbodiimide groups is 10 on average.

The oligomeric carbodiimides of table 1 were compounded in PET with assistance of a Mini extruder at 280° C. in an amount of 0.3 wt % based on the total amount of PET and oligomeric carbodiimide. Acid numbers are measured after 2 to 5 minutes' residence time in the extruder and compared with values resulting for an extruded PET without additives at the same times. The acid numbers are obtained by titrating the particular PET solution in the solvent mixture of chloroform/cresol.

The oligomeric carbodiimides of table 2, which are not functionalized according to the present invention, were enlisted for comparative tests.

TABLE 2

Structures of nonfunctionalized carbodiimides (CDI5-8)

| oligomeric carbodiimide group | name | end group |
|---|---|---|
| [structure: aromatic oligomeric carbodiimide based on tetramethylxylylene diisocyanate with R urethane end groups, repeat unit n] | CDI5 | R = methylpolyglycol 520 + methyldiglycol |
| | CDI6 | R = methylglycol |
| | CDI7 | R = 2-ethylhexanol |

TABLE 2-continued

Structures of nonfunctionalized carbodiimides (CDI5-8)

| oligomeric carbodiimide group | name | end group |
|---|---|---|
| (structure shown) | CDI8 | R = $(CH_2CH_2)nOCH_3$ |

The n value in the oligomeric carbodiimide groups is 10 on average.

Table 3 shows the results of measuring the acid numbers after 2 min and 5 min for different CDI quantities used.

| Name | Acid number change after 2 min [%] with 0.3% of CDI | Acid number change after 2 min [%] with 0.6% of CDI | Acid number change after 5 min [%] with 0.3% of CDI |
|---|---|---|---|
| CDI1 | −5 | −10 | — |
| CDI2 | −10 | −6 | — |
| CDI3 | −15 | — | −10 |
| CDI4 | −22 | −67 | — |
| CDI5 | +28 | — | −18 |
| CDI6 | +12 | −33 | −33 |
| CDI7 | +12 | −47 | −10 |
| CDI8 | +10 | +2.5 | −2 |

In the case of the nonfunctionalized oligomeric carbodiimides, the number of acid groups rises during the first two minutes of extrusion and then decreases in the period from two to five minutes due to the action of the oligomeric carbodiimides (CDI5-8).

In the case of the functionalized carbodiimides (CDI1-4) the number of acid groups starts to decrease during the first two minutes of extrusion and remains at a low level.

Example 3

Hydrolysis Stabilizer

Table 4 shows the results of viscosity measurements (VN: viscosity number) on a number of PBT (Ultradur® 84520) samples extruded with various additives in a Mini extruder at 280° C. for 2 minutes. VN was measured before and after storage at 110° C. and 100% relative humidity. The VN measurements (units in mg/l) were performed using a micro Ubbelohde capillary viscometer and a 1:1 mixture of phenol and o-dichlorobenzene as solvent. The values between parentheses identify the deviations (in percent) from the original PBT viscosity number (PBT VN) before storage directly after extrusion without additives (VN=121 mg/l).

TABLE 4

|  | before storage | after two days | after five days |
|---|---|---|---|
| PBT VN ref. [ml/g] | 121 | 96 (−21) | 61 (−49) |
| CDI1 (1 wt %) | 155 (+29) | 145 (+20.5) | 117 (−3) |
| CBC | 128 (+15) | 99 (−5.5) | 51 (−36) |
| CDI8 | 142 (+3) | 117 (−20) | 79 (−59) |
| CDI8 + CBC | 145 (+17) | 139 (+12) | 107 (−14) |

CBC: 1,1-carbonylbiscaprolactam.
The first sample with additives comprises 1 wt % of CDI1 based on the total amount of PBT and CDI1.
The other samples comprise a molar amount of caprolactam or carbodiimide groups which is equivalent to this 1 wt % CDI1.

It is clearly apparent from table 4 that the oligomeric carbodiimides (CDI) have a distinct suppressing effect on the hydrolysis of the polymer and as a result the polymers have a viscosity close to the original value even after a storage period of five days. Functionalized oligomeric carbodiimides (CDI1) suppress the hydrolysis to a greater extent than a mixture of the constituent parts (CDI8+CBC) which is equivalent in molar terms.

Table 5 shows the results of viscosity measurements on a number of poly(butylene adipate-co-terephthalate) samples (Ecoflex® FBX 7011). The additives were compounded with Ecoflex® FBX 7011 at 180° C. for 2 minutes and then press molded into plaques and stored in water at 60° C. for 24 days. The viscosity numbers were determined after each of 3, 11, 17 and 24 days and the results reported in table 5. The values between parentheses identify the deviations (in percent) from the original Ecoflex® FBX 7011 viscosity number before storage directly after extrusion without additives (VN=165 mg/l).

| Vn [ml/g] | before storage | Water storage at 60° C. [days] | | | |
|---|---|---|---|---|---|
|  |  | 3 | 11 | 17 | 24 |
| Ecoflex (ref.) | 165 | 156 (−5) | 126 (−23) | 113 (−31) | 90 (−45) |
| 0.2 wt % of CDI4 | 174 (+5) | 163 (−1) | 142 (−13) | 127 (−23) | 111 (−32) |
| 0.4 wt % of CDI4 | 173 (+4) | 168 (+2) | 147 (−10) | 129 (−21) | 114 (−30) |
| 0.6 wt % of CDI4 | 174 (+5) | 166 (+0.5) | 143 (−13) | 122 (−26) | 104 (−36) |
| 0.2 wt % of CDI2 | 173 (+5) | 162 (−2) | 137 (−17) | 117 (−29) | 102 (−38) |
| 0.4 wt % of CDI2 | 181 (+10) | 174 (+5) | 150 (−9) | 137 (−16) | 116 (−29) |
| 0.6 wt % of CDI2 | 198 (+20) | 204 (+24) | 183 (+10) | 177 (+7) | 158 (+4) |
| 0.2 wt % of CDI3 | 174 (+5) | 163 (−1) | 141 (−14) | 122 (−26) | 99 (−40) |

-continued

| Vn [ml/g] | before storage | Water storage at 60° C. [days] | | | |
|---|---|---|---|---|---|
| | | 3 | 11 | 17 | 24 |
| 0.4 wt % of CDI3 | 179 (+8) | 175 (+6) | 152 (−8) | 133 (−19) | 115 (−30) |
| 0.6 wt % of CDI3 | 186 (+13) | 181 (+10) | 166 (+0.5) | 144 (−12) | 135 (−18) |
| 0.4 wt % of CDI1 | 189 (+15) | 178 (+8) | 153 (−7) | 136 (−17) | 120 (−27) |
| 0.4 wt % of CDI8 | 173 (+5) | 165 (0) | 141 (−14) | 122 (−26) | 101 (−38) |

Oligomeric carbodiimides comprising at least one heterocyclic end group (CDI1, CDI2, CDI3, CDI4) exhibit an improved stabilizing effect over the oligomeric carbodiimide without heterocyclic end group (CDI8).

Example 4

Acid Numbers of PET: Combination with Chain Extender

| Chain extender with epoxy functionality (Joncryl ® ADR 4300) | CDI | Acid number change after 2 min [%] | Acid number change after 5 min [%] |
|---|---|---|---|
| 0.2 | | −2.2 | — |
| 0.4 | | −17.0 | — |
| | 0.2 (CDI 8) | +7.6 | +4.1 |
| | 0.4 (CDI 8) | +6.8 | −8.3 |
| | 0.2 (CDI 1) | −11 | — |
| | 0.4 (CDI 1) | −32.2 | — |
| 0.2 | 0.2 (CDI 8) | −14.1 | — |
| 0.2 | 0.4 (CDI 8) | −12.6 | — |
| 0.2 | 0.2 (CDI 1) | −23.3 | — |
| 0.2 | 0.4 (CDI 1) | −48.5 | — |

The amounts of chain extender and oligomeric carbodiimide are based on the total amount of PET, chain extender and oligomeric carbodiimide. Acid number change relates to the acid number of PET without chain extender and oligomeric carbodiimides, measured 2 min after extrusion.

The reference values without chain extender (with oligomeric carbodiimide only) were repeated to ensure comparability of results. They are in accord with the results of table 3. The combination of oligomeric carbodiimides with chain extender displays enhanced activity on the part of the oligomeric carbodiimides. The effect due to this combination is greater than the sum of the individual effects of the oligomeric carbodiimides and the chain extender alone.

We claim:

1. A process for stabilizing polymers against hydrolysis, the process comprising adding an effective amount of an oligomeric carbodiimide, comprising a heterocyclic end group, and a chain extender to a polymer, wherein the oligomeric carbodiimide is a compound represented by formula (I):

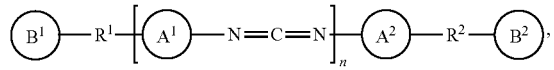

wherein:
A$^1$, A$^2$ are each independently, identically or differently, hydrocarbon groups having 2 to 20 carbon atoms;
B$^1$, B$^2$ are each independently, identically or differently:
R$^3$—(O—CH$_2$—CHR$^4$)$_m$—O—*,

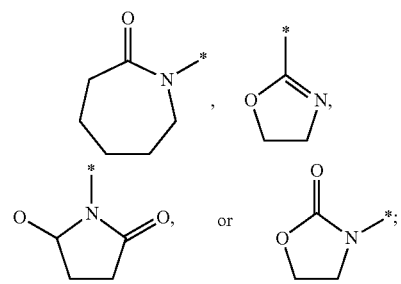

R$^1$, R$^2$ are each independently, identically or differently:

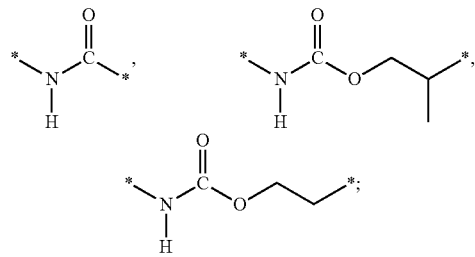

n is an integer from 2 to 100; and
A$^1$, A$^2$, B$^1$ and B$^2$ are each optionally substituted at any position by C$_1$-C$_{20}$-alkyl, C$_2$-C$_{20}$-alkenyl, C$_2$-C$_{20}$-alkynyl, C$_1$-C$_{20}$-alkoxy, carbonyl oxygen (=O) or halogen,
with the proviso that at least one B$^1$ or B$^2$ substituent is a heterocyclic end group.

2. The process according to claim 1, wherein A$^1$, A$^2$ each comprise, independently, identically or differently, the hydrocarbon groups:

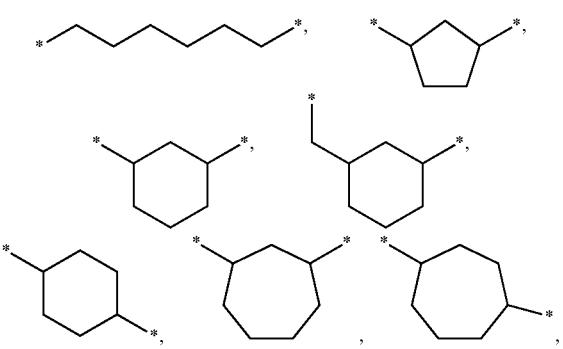

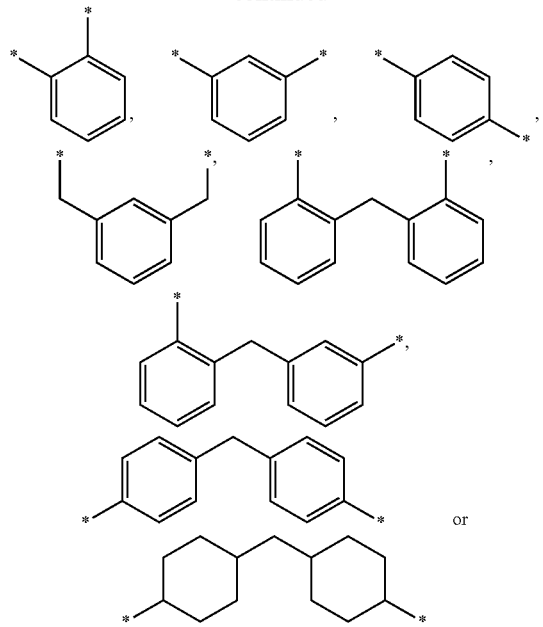

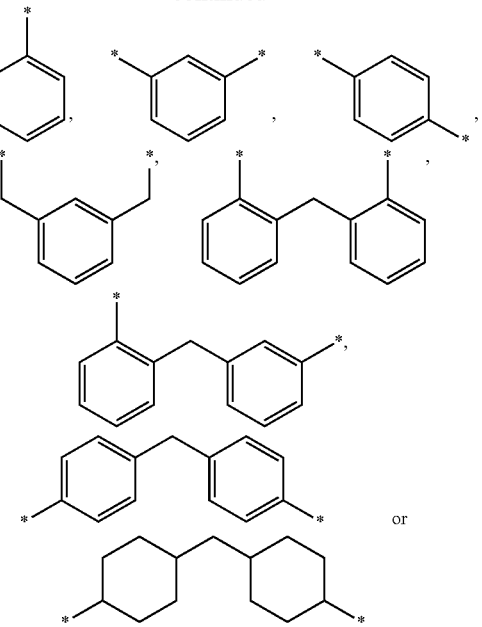

3. The process according to claim 1, wherein the polymer is a polycondensate or a polyaddition.

4. The process according to claim 3, wherein the polymer is at least one selected from the group consisting of a polyester, a polyamide, a polyurethane, a polycarbonate, and copolymers thereof.

5. The process according to claim 3, wherein the polymer is PET, PBT, PEN, PC, ABS, a biodegradable aliphatic-aromatic copolyester, a biopolymer or PA6.

6. The process according to claim 1, wherein the oligomeric carbodiimide is added in an amount of 0.01 to 10 wt %, based on a total amount of polymer and oligomeric carbodiimide.

7. An oligomeric carbodiimide of the formula (II):

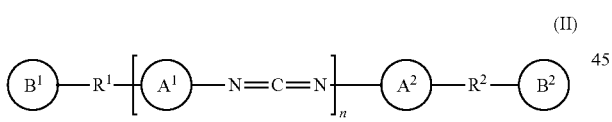

wherein:

$A^1$, $A^2$ each, independently, identically or differently, comprise:

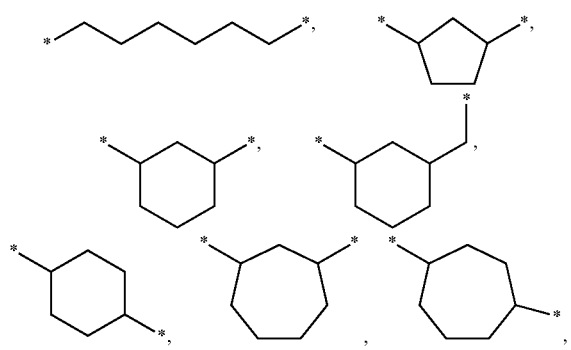

$B^1$, $B^2$ each independently, identically or differently, represent:

$R^3$—(O—$CH_2$—$CHR^4$)$_m$—O—*,

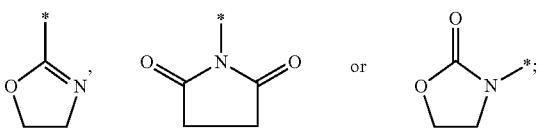

$R^1$, $R^2$ each independently, identically or differently, represent:

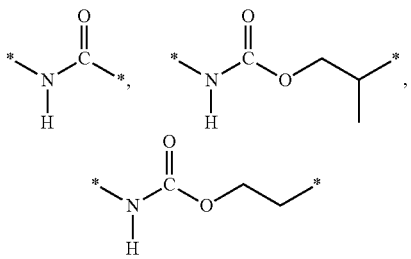

n is an integer from 2 to 100;
$R^3$ is $C_1$-$C_{20}$-alkyl, $C_2$-$C_{20}$-alkenyl, or $C_2$-$C_{20}$-alkynyl;
$R^4$ is H, $C_1$-$C_{20}$-alkyl, $C_2$-$C_{20}$-alkenyl, or $C_2$-$C_{20}$-alkynyl; and
m is an integer from 1 to 500,
such that $A^1$, $A^2$, $B^1$ and $B^2$ are optionally substituted at any position by $C_1$-$C_{20}$-alkyl, $C_2$-$C_{20}$-alkenyl, $C_2$-$C_{20}$-alkynyl, $C_1$-$C_{20}$-alkoxy, carbonyl oxygen (=O) or halogen, and
with the proviso that at least one $B^1$ or $B^2$ substituent is a heterocyclic end group.

8. A mixture, comprising the oligomeric carbodiimide according to claim 7 and a polymer.

9. The mixture according to claim 8, wherein the polymer is a polycondensate or a polyaddition product.

10. The mixture according to claim 8, wherein the polymer is at least one selected from the group consisting of a polyester, a polyamide, a polyurethane, a polycarbonate, and copolymers thereof.

11. The mixture according to claim 8, wherein the polymer is PET, PBT, PEN, PC, ABS, a biodegradable aliphatic-aromatic copolyester, a biopolymer or PA6.

12. The mixture according to claim 8, wherein the oligomeric carbodiimide is present in an amount of 0.01 to 10 wt %.

13. A mixture, comprising an oligomeric carbodiimide comprising a heterocyclic end group and a chain extender, wherein the oligomeric carbodiimide is a compound represented by formula (I):

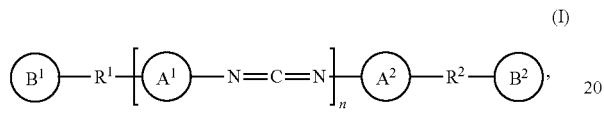
(I)

wherein:
A$^1$, A$^2$ are each independently, identically or differently, hydrocarbon groups having 2 to 20 carbon atoms;
B$^1$, B$^2$ are each independently, identically or differently:
R$^3$—(O—CH$_2$—CHR$^4$)$_m$—O—*,

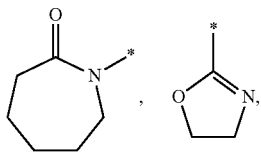

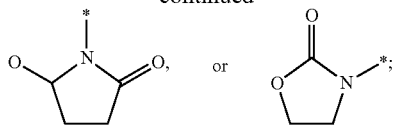

R$^1$, R$^2$ are each independently, identically or differently:

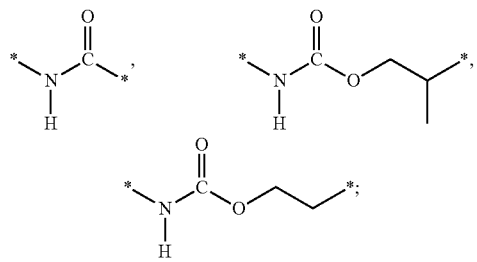

n is an integer from 2 to 100; and
A$^1$, A$^2$, B$^1$ and B$^2$ are each optionally substituted at any position by C$_1$-C$_{20}$-alkyl, C$_2$-C$_{20}$-alkenyl, C$_2$-C$_{20}$-alkynyl, C$_1$-C$_{20}$-alkoxy, carbonyl oxygen (=O) or halogen,
with the proviso that at least one B$^1$ or B$^2$ substituent is a heterocyclic end group.

14. The mixture according to claim 13, further comprising a polymer.

15. A process for stabilizing polymers against hydrolysis, the process comprising adding an effective amount of the oligomeric carbodiimide of claim 7 and a chain extender to a polymer.

* * * * *